(12) United States Patent
Augier et al.

(10) Patent No.: US 10,646,795 B2
(45) Date of Patent: May 12, 2020

(54) PERIPHERAL DISTRIBUTION OR COLLECTION SYSTEM FOR A SIMULATED MOVING BED SEPARATION METHOD USING N COLUMNS IN SERIES

(71) Applicant: IFP Energies nouvelles, Rueil-Malmaison (FR)

(72) Inventors: Frederic Augier, Saint Symphorien D'Ozon (FR); Aude Royon-Lebeaud, Lyons (FR); Damien Leinekugel Le Cocq, Lyons (FR); Alexandre Vonner, Mions (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/306,306

(22) PCT Filed: May 5, 2017

(86) PCT No.: PCT/EP2017/060835
§ 371 (c)(1),
(2) Date: Nov. 30, 2018

(87) PCT Pub. No.: WO2017/207217
PCT Pub. Date: Dec. 7, 2017

(65) Prior Publication Data
US 2019/0126166 A1    May 2, 2019

(30) Foreign Application Priority Data

May 30, 2016    (FR) ...................... 16 54864

(51) Int. Cl.
*B01D 1/02*    (2006.01)
*B01D 1/14*    (2006.01)
(Continued)

(52) U.S. Cl.
CPC .......... *B01D 15/1842* (2013.01); *B01D 1/02* (2013.01); *B01D 1/14* (2013.01); *B01D 15/14* (2013.01);
(Continued)

(58) Field of Classification Search
None
See application file for complete search history.

(56) References Cited

U.S. PATENT DOCUMENTS 2,748,497 A * 6/1956 Berg .................. B01J 8/003
                                                       34/168
5,846,411 A * 12/1998 Harter ............... B01D 15/1842
                                                       210/198.2
(Continued)

FOREIGN PATENT DOCUMENTS

EP    842687 A1    5/1998
FR    2740052 A1   4/1997
(Continued)

OTHER PUBLICATIONS

International Search Report PCT/EP2017/060835 dated Jul. 7, 2017.

*Primary Examiner* — Tam M Nguyen
(74) *Attorney, Agent, or Firm* — Millen, White, Zelano and Branigan, P.C.

(57) ABSTRACT

The present invention describes a device for distributing incoming fluid or for collecting fluid being discharged from a column forming part of an assembly of N columns in series intended to be used in a simulated moving bed separation process. The present device can be used to very substantially reduce the non-selective volumes at each column, while at the same time providing the flow with good synchronicity.

10 Claims, 6 Drawing Sheets

(51) Int. Cl.
*B01D 15/14* (2006.01)
*B01D 15/18* (2006.01)
*B01D 15/22* (2006.01)
*G01N 30/46* (2006.01)
*G01N 30/44* (2006.01)
*G01N 30/60* (2006.01)
*C07C 7/12* (2006.01)
*C10G 25/00* (2006.01)
*G01N 30/38* (2006.01)
*B01D 3/00* (2006.01)

(52) U.S. Cl.
CPC ......... *B01D 15/1871* (2013.01); *B01D 15/22* (2013.01); *C07C 7/12* (2013.01); *C10G 25/00* (2013.01); *G01N 30/44* (2013.01); *G01N 30/461* (2013.01); *G01N 30/6017* (2013.01); *B01D 3/008* (2013.01); *B01D 2215/024* (2013.01); *G01N 2030/386* (2013.01)

(56) References Cited

U.S. PATENT DOCUMENTS

| | | | |
|---|---|---|---|
| 5,972,214 | A | 10/1999 | Callebert |
| 6,015,491 | A | 1/2000 | Renard |
| 7,288,200 | B1 | 10/2007 | Hotier |
| 2016/0271520 | A1* | 9/2016 | Hofmann ................ B01D 15/22 |
| 2019/0291022 | A1* | 9/2019 | Hofmann ........... G01N 30/6026 |

FOREIGN PATENT DOCUMENTS

| | | | |
|---|---|---|---|
| FR | 2794663 | A1 | 12/2000 |
| WO | 2013089774 | A1 | 6/2013 |

* cited by examiner

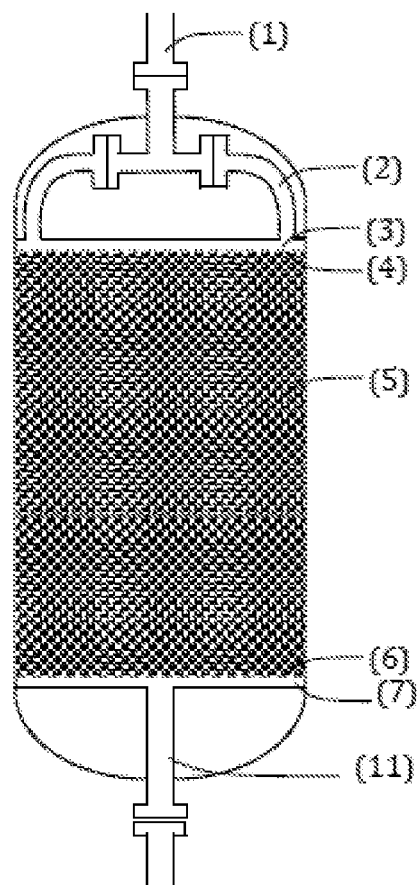
FIG 1bis

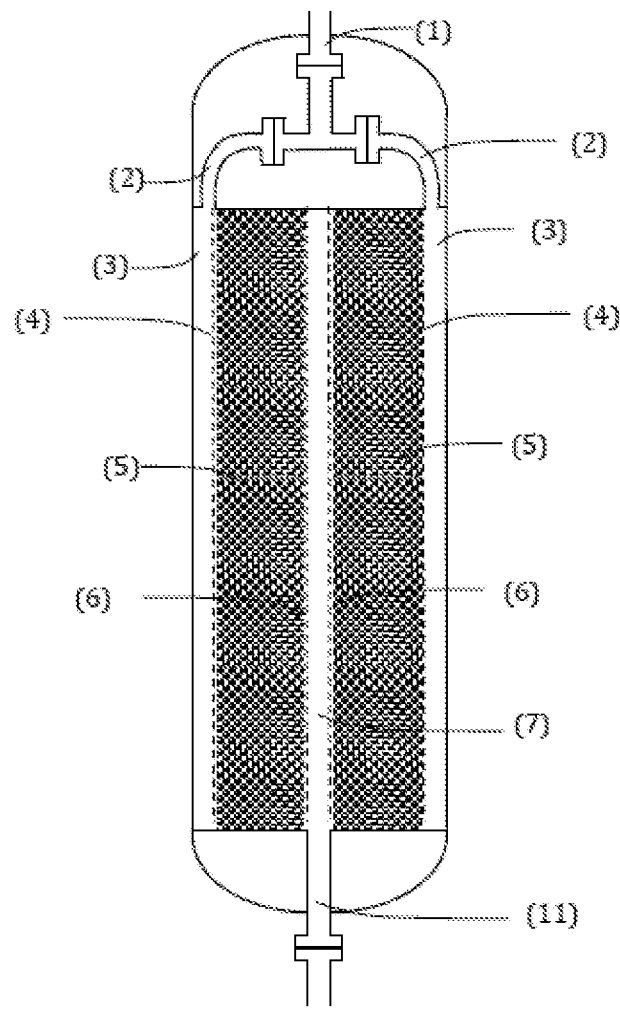
FIG 2 bis

PERIPHERAL DISTRIBUTION OR COLLECTION SYSTEM FOR A SIMULATED MOVING BED SEPARATION METHOD USING N COLUMNS IN SERIES

CONTEXT OF THE INVENTION

The invention relates to a novel device for distribution and collection of fluids within a system with N columns in series employing a flow of said fluids in a medium of solid particles known as a granular medium.

A system of N columns in series is known as a concatenation of N distinct or stacked columns (i.e. arranged within a common envelope). Each column houses a bed of granular medium in which the principal fluid flows. The N columns are connected together via a network of conduits which can be used as appropriate for injection/mixing or withdrawal of a secondary fluid, these possible injections and withdrawals taking place between the columns. The N columns operate in series in the sense that the fluid leaving one column enters into the following column.

The present invention concerns a device for the distribution of fluid entering into a column of the series in order to distribute it over the whole of the section of the granular bed.

The present invention also concerns a device which may be used to collect the principal fluid at the bottom of the bed over the entire section of the column in order to supply it to the inter-column conduit which can be used to transfer said fluid to the next column.

The invention essentially consists of an arrangement of the distribution zone located at the head of the column or the collection zone located at the bottom of the column.

The invention can be used to even out, in an advantageous manner, the distribution of the dwell times for the fluid in a column between the two zones which are said to be non-selective, i.e. outside the granular medium whatever the constitution of the distribution zone at the head of the bed and the collection zone at the bottom of the bed, while substantially minimizing the volumes of the zones which are termed non-selective.

In fact, the invention concerns simulated moving bed (SMB) separation processes, in which the synchronicity of all the particles of fluids within the bed and within the injection/collection network is particularly critical in order to ensure the high levels of purity and yields required for the process. This will be abbreviated below to "fluid synchronicity".

The term "fluid synchronicity" means that if the section of the column is mentally divided into a multiplicity of fluid channels which move in parallel, each fluid channel must, as far as is possible, have the same dwell time from its entry into the column to its discharge.

Furthermore, any increase in the volumes of the non-selective zones induces an unwanted increase in the "pump around" flow rates in the unit for the same levels of performance.

BRIEF DESCRIPTION OF THE FIGURES

The set of figures depicts a downflow mode, but, as will be explained below, the case of an upflow mode is also encompassed by the invention and will be strictly symmetrical as regards the flow.

FIG. 1bis represents a variation of the column in accordance with the invention, in which injection into the bed is carried out by means of a network of peripheral conduits which supplies the distribution channel.

FIG. 2b is represents a diagrammatic view of the column in a radial fluid flow variation with the supply network in accordance with the invention.

EXAMINATION OF THE PRIOR ART

Figures 1, 1A:
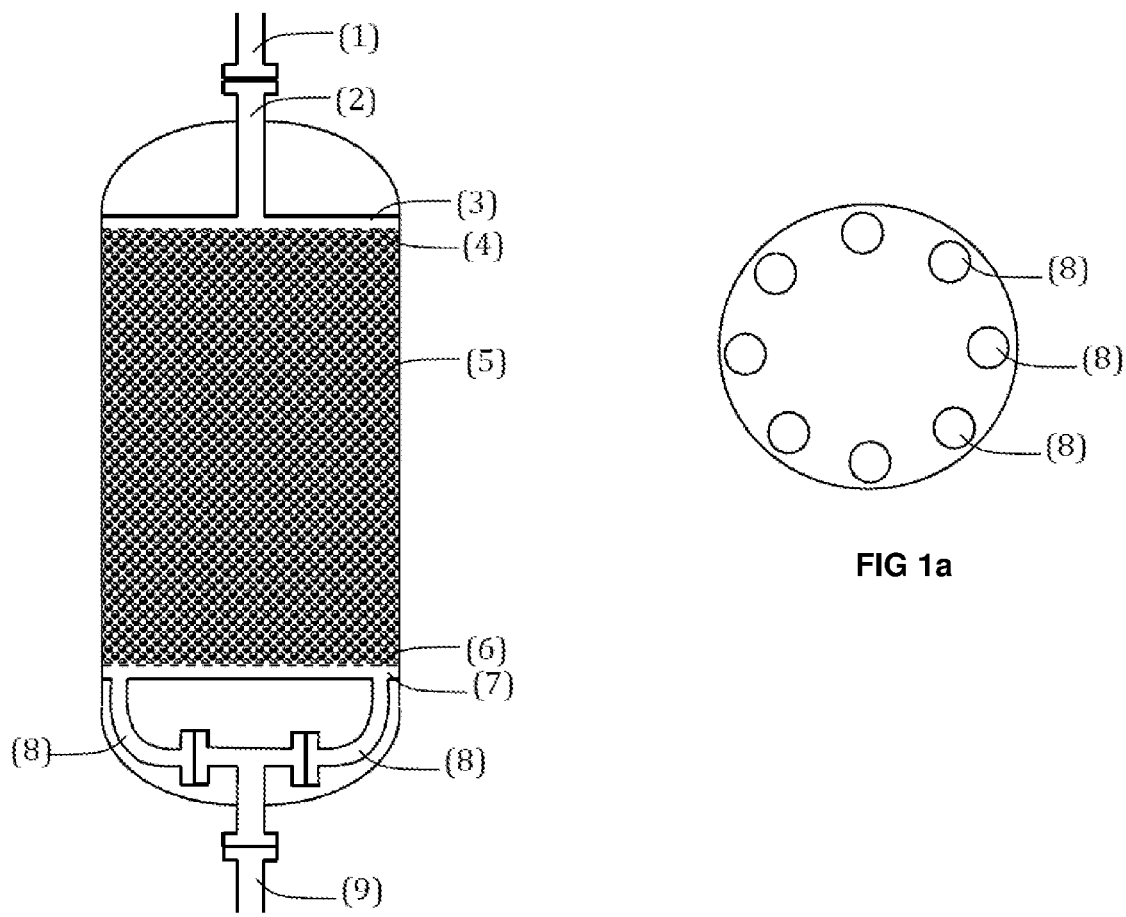
FIG. 1 represents a diagrammatic view of the whole column with an axial flow of fluids with its fluid distribution device at the head and its collection device at the bottom.
FIG. 1a is a top view allowing the placement of the collection conduits (8) to be viewed.

The prior art provides know-how as to the dimensions to be used for a distributor for a multi-stage column, i.e. constituted by multiple plates disposed along a substantially vertical axis, each plate supporting a bed of granular solid.

The patents EP 0 074 815 and US 2006/0108274 A1 in particular provide examples of distribution/mixing devices used in the case of simulated moving bed adsorption for a multi-stage column. Those devices carry out the successive functions of collection of the principal fluid coming from the upstream bed, mixing the principal fluid with the secondary fluid, and redistribution of the mixture towards the downstream bed.

Those patents describe dividing the section of the column into radial sectors or panels.

The prior art also teaches the importance of ensuring good synchronicity in the distribution system in order to obtain the required performances as regards separation.

In particular, the patent FR 2 933 000 proposes adding a dwell time compensation element, namely a baffle, to the non-selective zone just before or just after the distributor plate at the inlet to the column.

The document by Silva M, Rodrigues A and Mota J "Effect of dead volumes on the performance of an industrial-scale simulated moving bed parex unit or p-Xylene purification", published in the AIChE Journal in January 2016, vol 62, n° 1, emphasizes the importance of reducing the non-selective volumes because increasing these volumes results in a drop in purity and an increase in the consumption of desorbant.

Operating a simulated moving bed with a system of N columns in series ensures that the injections and collections as well as mixing are guaranteed to occur at a single point between two columns in the network. Thus, the person skilled in the art knows that problems with flushing could be overcome as in this manner, it minimizes volumes which are not flushed by the pump around flow.

BRIEF DESCRIPTION OF THE INVENTION

The present invention may be defined as a device for distributing fluid in a column comprising a bed of granular solid, said solid being an adsorbent solid, said column forming part of an assembly of N columns operating in series. The value of N is generally in the range 4 to 24, preferably in the range 6 to 15.

This device is particularly suitable for the simulated moving bed separation process, because it can be used to substantially reduce the volumes which are said to be non-selective, as will be illustrated in the comparative example forming part of the present application. In the remainder of the text, the term "incoming fluid" will be used to denote the fluid entering the column and the term "outgoing fluid" will be used to denote the fluid being discharged from the column.

The process using the present device generally makes use of a plurality of columns in series, each column using the device in accordance with the invention, either as a means for introducing incoming fluid, or as a means for collection of outgoing fluid. For this reason, the text will refer to a device for the distribution of incoming fluid or for collecting outgoing fluid and sometimes, more simply, it will refer to a distribution or collection device.

The columns constituting the series of N columns may have an axial or radial flow of fluid within the granular bed.

Any series of N columns, each column being provided with a device in accordance with the invention, either as a means for introducing incoming fluid, or as a means for collecting outgoing fluid, is included in the scope of the present invention.

More precisely, the device for the distribution of incoming fluid or for collecting outgoing fluid in a column provided with a bed of adsorbent granular solid, said column forming part of a series of N columns disposed in series, may be defined as a device in which the distribution of fluid entering at the level of a column is carried out by means of a plurality of evenly distributed peripheral conduits (2) starting from a single substantially central supply conduit, or in fact the collection of outgoing fluid is carried out by means of peripheral conduits (8) evenly distributed over the section of the column and merging into a single substantially central conduit. The throughput velocity in the channels for injecting incoming fluid or for collecting outgoing fluid is in the range 1 to 6 m/s, and the number of peripheral conduits (2) or (8) is between 4 and 20, preferably between 6 and 12.

In the variation in which the flow of fluid in each column of the series is axial, the principal dimensions of each column are as follows:
  a diameter in the range 1 to 15 m, preferably in the range 7 to 12 m,
  a height for the granular bed in the range 0.2 to 1.5 m, preferably in the range 0.4 to 1 m.

In the variation in which the flow of fluid in each column is radial from the periphery towards the centre, the principal dimensions of each column are as follows:
  a diameter of between 3 and 15 m,
  a height which allows a section in the range 1 to 200 m², preferably in the range 20 to 80 m², to be developed, said section being calculated as that of the cylinder with a height which is the height of the granular bed and with a radius which is any radius included between the radius of the incoming collector and the radius of the central collector,
  the thickness of the granular bed being between 0.2 and 1.5 m, and preferably between 0.4 and 1 m.

More precisely, the present invention may thus be defined as a device for the distribution of incoming fluid or for the collection of outgoing fluid in one or more columns provided with a bed of granular solid, in which device:
  fluid is distributed by means of a plurality of peripheral conduits which are evenly distributed about a single substantially central supply conduit, the number of peripheral conduits being between 4 and 20, preferably between 6 and 12,
  or indeed the outgoing fluid is collected by means of peripheral conduits evenly distributed over the section of the column and which merge into a single substantially central conduit, the number of peripheral conduits being between 4 and 20, preferably between 6 and 12.

The present device is of particular application to a simulated moving bed separation process using a plurality of columns disposed in series. The number of columns in series, N, is from 4 to 24, preferably from 6 to 15.

In accordance with a first variation, shown in FIGS. 1 and 1a, the simulated moving bed process using the collection device in accordance with the invention may be described as follows:
  movement of fluid inside the bed of granular solid is axial, and injection into the bed is carried out by means of a conduit (2) substantially centred on the vertical axis of the column, which supplies the horizontal distribution channel (3), the bed of granular solid (5) then being supplied from said distribution channel (3) through a screen (4) and the fluid flowing through the granular bed (5) in a substantially vertical direction, the fluid then being collected below the screen (6) starting from a collection channel (7) via peripheral conduits (8), and the whole of the flow being collected in a single evacuation conduit (9) substantially centred on the vertical axis of the column, the throughput velocity of the fluid being discharged into the peripheral conduits (8) being in the range 1 to 6 m/s.

In accordance with a second variation, shown in FIG. 1bis, the simulated moving bed process using the distribution device in accordance with the invention may be described as follows: movement of fluid inside the bed of granular solid is axial, and the fluid is introduced into the bed by means of a network of peripheral conduits (2) which supply the distribution channel (3), then through a screen (4), the fluid flowing inside the granular bed (5) in a substantially vertical direction, the outgoing fluid being collected from the collection channel (7) by means of a single conduit (11) substantially centred on the vertical axis of the column, the throughput velocity of the fluid entering the peripheral conduits (2) being in the range 1 to 6 m/s.

The direction of the axial flow may be vertical from the top or vertical from the bottom. The collection device in the downflow mode is then the same as the distribution device in upflow mode.

In accordance with a third variation, shown in FIGS. 2 and 2a, the process using the distribution device in accordance with the invention may be described as follows: movement of the fluids inside the bed of granular solid is radial, the fluid being introduced at the centre of the column via the central channel (2) then passing through the granular bed (5) from the centre towards the periphery where it is collected in the peripheral zone (7) which brings the liquid, via peripheral conduits (8), towards the evacuation conduit (9) which is substantially centred on the axis of the column, the throughput velocity of the fluid being discharged in the peripheral conduits (8) being in the range 1 to 6 m/s.

In accordance with a fourth variation, shown in FIG. 2b is, the process using the distribution device in accordance with the invention may be described as follows: movement of the fluids inside the bed of granular solid is radial, the fluid being introduced into the granular bed from a central conduit (1) which is divided into a plurality of peripheral conduits (8) for supplying the granular bed (5), the fluid passing through said bed from the periphery towards the centre where it is collected in the central channel (7) then evacuated via the conduit (11) which is substantially centred on the vertical axis of the column, the throughput velocity of the fluid entering the peripheral conduits (8) being in the range 1 to 6 m/s.

The simulated moving bed separation process using the device in accordance with the invention may be such that the feed to be separated is any mixture of aromatic compounds containing 7 to 9 carbon atoms.

The simulated moving bed separation process using the device in accordance with the invention may be such that the feed to be separated is a mixture of normal and iso-paraffins.

The simulated moving bed separation process using the device in accordance with the invention may be such that the feed to be separated is a mixture of normal and iso-olefins.

The simulated moving bed separation process using the device in accordance with the invention may be such that the principal fluid passing through said device has a density in the range 600 to 950 kg/m$^3$ and a viscosity in the range 0.1 to 0.6 cPo.

DETAILED DESCRIPTION OF THE INVENTION

The problem to be solved by the present invention is that of limiting the differences in dwell times in the non-selective zones of a system of N columns operating in series, which differences have a deleterious effect on the separation performances, while at the same time minimizing the volumes of said non-selective zones (for simplicity, hereinafter termed "non-selective volumes") which causes an undesirable increase in the "pump around" flow rate of the unit for the same levels of performance as a system which does not have a non-selective zone.

The invention pertains to a system which can be used to ensure good fluid synchronicity in the distribution/collection system on the scale of the complete section of the column, and which also generates a low non-selective volume while at the same time utilizing the network of distribution and collection conduits in a manner which is sufficient. The term "synchronicity" means the fact that each incoming fluid element has approximately the same dwell time in the column as the other incoming elements. This means that the distribution of the dwell times is a Gaussian curve with a standard deviation which is as reduced as far as possible. In practice, it is assumed that the synchronicity is correct if the dwell time dispersion is plus or minus 10% with respect to the mean value.

The columns in accordance with the invention may be organized in accordance with two flow modes:

An axial mode, in which the flow inside the granular bed essentially occurs along the vertical axis of the column, from top to bottom or from bottom to top.

A radial mode, in which the flow inside the granular bed essentially occurs from the periphery towards the centre of the column, or from the centre of the column towards the periphery.

The dimensions of the columns are as follows, depending on the mode of flow:

For an axial mode, a diameter between 1 and 15 m, preferably between 7 and 12 m. The height of the granular bed is between 0.2 and 1.5 m, preferably between 0.4 and 1 m.

For a radial mode, a diameter between 3 and 15 m, a height allowing a section in the range 1 to 200 m$^2$ to be developed, preferably in the range 20 to 80 m$^2$. The section of the granular bed is defined as that of the cylinder with a height which is the height of the granular bed and with a radius which is any radius in the range between the radius of the cylinder corresponding to the incoming collector and the radius of the cylinder corresponding to the central collector. The section of the granular bed thus varies as a function of the radius from the incoming collector to the discharge collector. The thickness of the granular bed is between 0.2 and 1.5 m, preferably between 0.4 and 1 m.

Injections and collections as well as mixing are carried out at a single point between two columns in the network (1).

In accordance with a first embodiment shown in FIG. 1, the bed is in axial mode and injection into the bed is carried out by means of a conduit (2) centred substantially on the vertical axis of the column, which feeds a horizontal channel distribution (3) via a jet.

The granular bed (5) is then fed from the distribution channel (3) through a screen (4).

The fluid flows through the granular bed (5) in a substantially vertical direction.

The fluid is then collected in the collection channel (7) below the screen (6).

The whole of the flow is collected by the network of peripheral collection conduits (8).

Collection is said to be peripheral because the points (8) for recovery of fluid being discharged from the collection channel (7) are at the periphery of said channel, as shown in the top view of FIG. 1a.

In accordance with a second embodiment, shown in FIG. 1bis, the bed is in axial mode and injection into the bed is carried out by means of a network of peripheral conduits which supply the distribution channel (3). Collection is carried out by means of a single conduit (11) centred on the column which collects the flow from the collection channel.

The columns may be concatenated in two ways:

Either the columns all have a distribution system in accordance with the invention, or they all have a collection system in accordance with the invention. It is also possible to concatenate the columns in an alternating manner, i.e. one column having a collection system in accordance with the invention, and the next column having a distribution system in accordance with the invention. The context of the present invention fully encompasses concatenating columns provided with a distribution or collection system in accordance with the invention.

The heights of the injection and collection channels are dimensioned such that the throughput velocity does not exceed a dimensioning velocity in the range 1 to 8 m/s at any point.

The number of conduits will be between 4 and 20, preferably between 6 and 12. The conduit sections will be dimensioned to ensure a fluid speed in the range 1 to 8 m/s.

Figures 2, 2A:
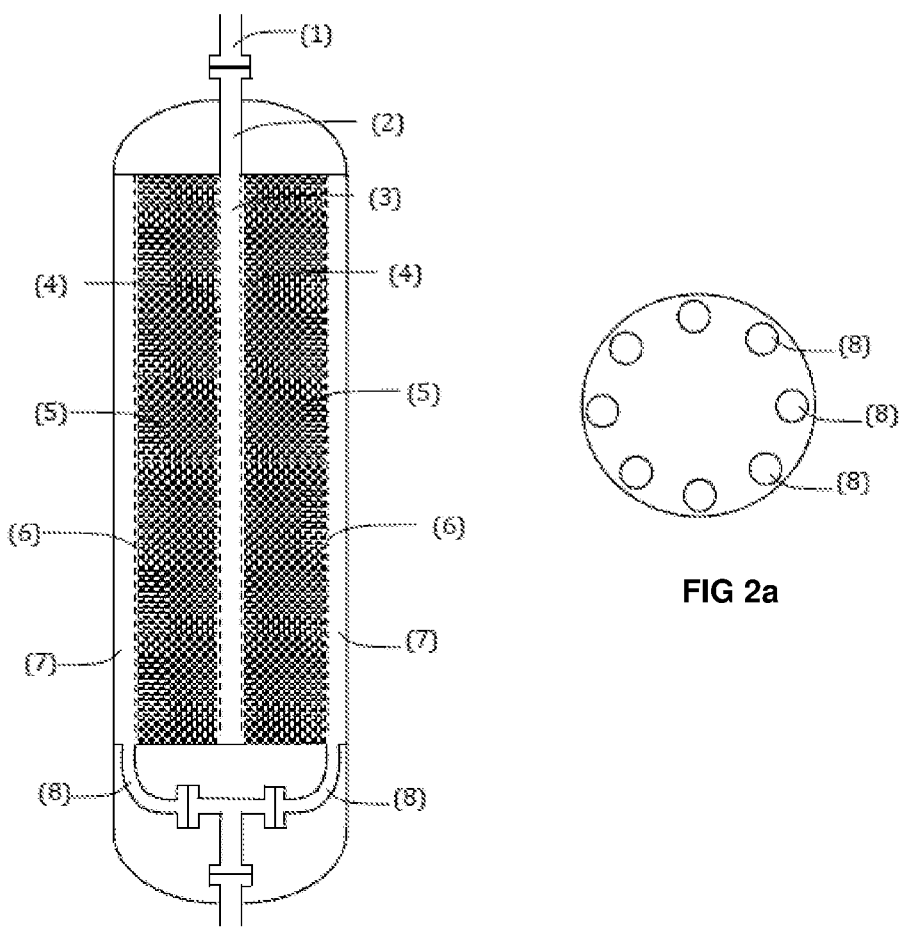
FIG. 2 represents a diagrammatic view of the column in a radial fluid flow variation with the collection network in accordance with the invention.
FIG. 2a is a top view showing the placement of the collection conduits (8).
Figure 3:
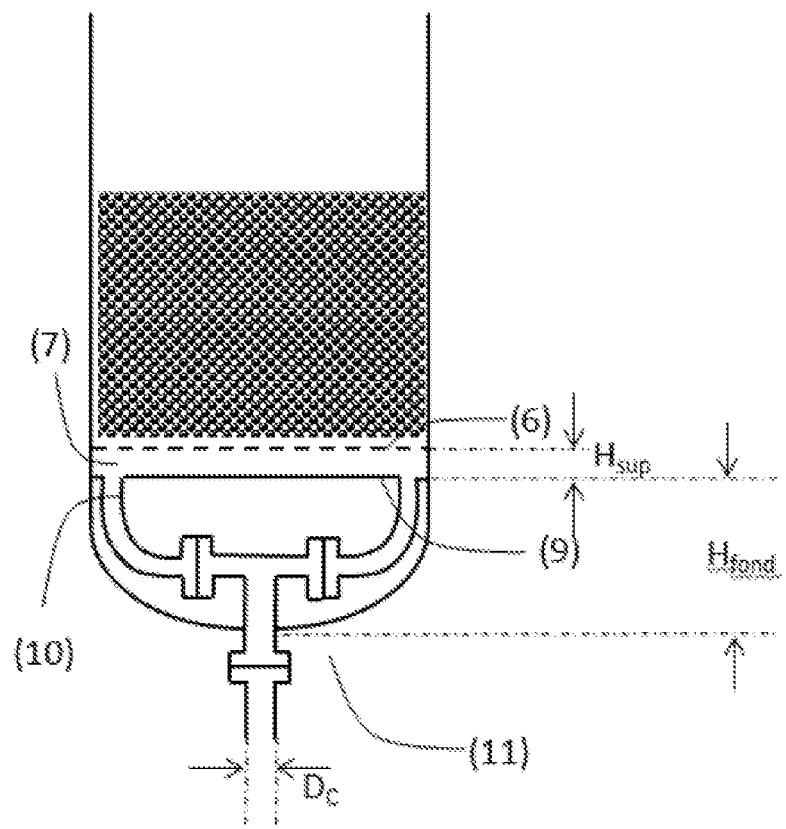
FIG. 3 represents a more detailed view of the bottom of the column of the invention and shows the dimensional parameters Hsup, Hfond and the diameter Dc of the conduit connecting one column to the next.

In accordance with a third embodiment, shown in FIG. 2, the bed is operated in radial mode and injection into the bed is carried out by means of a vertical conduit (2) or by means of an annular tube positioned substantially at the centre of the column. The liquid flows radially in the bed (5) from the centre towards the periphery of the bed, and is collected in the peripheral zones (7). The entire flow is collected by the network of conduits (8) located at the periphery which brings the outgoing fluid to the evacuation conduit (9).

In accordance with a fourth embodiment shown in FIG. 2bis, the bed is operated in radial mode and injection into the bed is carried out by means of a network of peripheral conduits. The liquid flows radially in the bed (5) from the periphery to the centre of the column and is collected in the central channel (7). The whole of the flow is collected via a hollow conduit or via an annular tube (11) positioned substantially at the centre of the column and recovering the outgoing fluid issuing from the central channel (7).

Examples in Accordance with the Prior Art and in Accordance with the Invention

Figure 4:
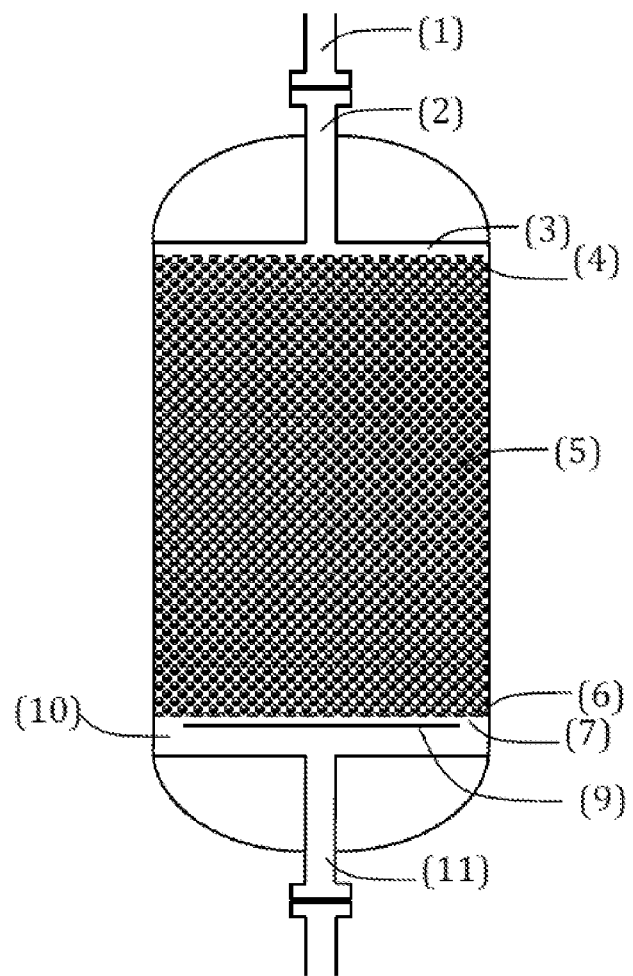
FIG. 4, which is in accordance with the prior art, represents a diagrammatic view of the entire column in a configuration which can be used to level out the dwell times of the non-selective zones using a baffle (9).

The aim of this comparative example is to provide values for the non-selective volumes and dispersion volumes in 3 cases:

a) the prior art, without compensation for the dwell time, b) the prior art, with compensation for the prior art using a baffle (9) as can be seen in FIG. 4, c) the present invention.

Consider a column 2 m in diameter comprising a granular bed 1 m high. The flow of fluid with a density of 725 kg/m$^3$ and viscosity of 0.2 cP occurs inside the column with a surface velocity of 2 cm/s. This surface velocity is calculated over the section of the column which is assumed to be free.

To dimension this column without compensating for the dwell time, in accordance with the layout of FIG. 4 without the baffle (9) in FIG. 4 (which corresponds to the prior art solution), the person skilled in the art will fix a maximum velocity in the distribution and collection channels and in the distribution and collection conduits, and this velocity will serve to dimension said channels and said conduits. In this example, a maximum velocity of 5 m/s was used. The resulting heights of the channels are 3.2 cm; the conduit diameter is 12.6 cm.

a) For dimensioning without compensation for the dwell time, the result is a non-selective volume (distribution and collection) of 0.21 m$^3$ and a dispersion of 9.4 s$^2$.

The prior art shown in patent FR 2 933 000 explains how to dimension a baffle in order to level out the dwell time distribution. The ratio between the annular section (passage of liquid between the edge of the baffle and the wall of the column) and the total section of the column is selected such as to be identical to that of the example of the patent, i.e. 8.3%. The baffle (9) thus has a diameter $L_c$ of 1.91 m. As can be seen in FIG. 4, with a baffle, there is an upper collection channel (7) and a lower channel (10). The heights required are 0.21 cm for the upper channel and 3.2 cm for the lower channel.

b) In the case of dimensioning with compensation for the dwell time using a baffle (9) in accordance with the prior art, the non-selective volume (distribution and collection) is 0.22 m$^3$ and the dispersion is 3.1 s$^2$.

c) In the case of the present invention, for the upper channel we used the same dimensioning criteria as in the prior art. The diameter of the 8 peripheral collection conduits (8), dimensioned using a maximum velocity criterion of 5 m/s, is 4.5 cm.

In the case of the dimensioning in accordance with the invention, this results in a non-selective volume (distribution and collection) of 0.13 m$^3$ and a dispersion of 3.2 s$^2$.

Thus, the present invention can save 40% of the non-selective volume while maintaining a substantial gain as regards the dispersion of the dwell time. Note that the reduction in the non-selective volume for an equivalent dispersion is an essential element in maintaining the performances of the simulated moving bed separation process.

|  | Volume of non-selective zones (m$^3$) | Dispersion of non-selective zones (s$^2$) |
|---|---|---|
| a) Dimensioning in accordance with prior art, no compensation | 0.21 | 9.4 |
| b) Dimensioning in accordance with prior art, with compensation | 0.22 | 3.1 |
| c) Dimensioning in accordance with the invention | 0.13 | 3.2 |

The invention claimed is:

1. A device for distributing fluid entering a column provided with a bed of adsorbent granular solid, said column forming part of a series of N columns disposed in series, in which device the distribution of fluid entering at the level of a column is carried out by means of a plurality of peripheral conduits (2) which are distributed evenly at the periphery of the column, connected to a single substantially central supply conduit (1), each peripheral conduit (2) supplying the distribution channel (3) followed downstream by a screen (4), the fluid flowing inside the granular bed (5) in a substantially vertical direction, the discharged fluid being collected from the collection channel (7) by means of a single conduit (11) which is substantially centred on the vertical axis of the column, the throughput velocity of the fluid entering the peripheral conduits (2) being in the range 1 to 6 m/s, and the flow of fluid in the column being axial, i.e. along the vertical axis of the column, the number of columns N in series being in the range 4 to 24, and preferably in the range 6 to 15, and the number of peripheral conduits (2) being between 4 and 20.

2. The device for distributing incoming fluid or for collecting fluid being discharged from a column with a bed of adsorbent granular solid as claimed in claim 1, in which the principal dimensions of each column are as follows:

a diameter in the range 1 to 15 m, preferably in the range 7 to 12 m, a height for the granular bed in the range 0.2 to 1.5 m.

3. A device for distributing fluid entering a column provided with a bed of adsorbent granular solid, said column forming part of a series of N columns disposed in series, in which device the distribution of fluid entering at the level of a column is carried out by means of a plurality of peripheral conduits (2) which are distributed evenly at the periphery of the column, connected to a single substantially central supply conduit (1), each peripheral conduit (2) supplying the distribution channel (3) followed downstream by a screen (4), the fluid flowing inside the granular bed (5) in a radial direction, from the periphery towards the centre of the column, and the throughput velocity of the fluid entering the peripheral conduits (2) being in the range 1 to 6 m/s, and the number of columns N in series being in the range 4 to 24, and preferably in the range 6 to 15, and the number of peripheral conduits (2) being between 4 and 20.

4. The device for distributing fluid entering a column provided with a bed of adsorbent granular solid as claimed in claim 3 in which, for a radial flow of fluid inside the column, the principal dimensions of each column are as follows:

a diameter of between 3 and 15 m, a height which allows a section in the range 1 to 200 m$^2$, preferably in the range 20 to 80 m$^2$, to be developed, said section being calculated as that of the cylinder with a height which is the height of the granular bed and with a radius which is any radius included between the radius of the incoming collector and the radius of the central collector, the thickness of the granular bed being between 0.2 and 1.5 m.

5. A simulated moving bed process using the distribution device as claimed in claim 1, in which the fluid is introduced into the bed by means of a conduit (1) which is centred substantially on the vertical axis of the column, which is divided into a plurality of peripheral conduits (2) distributed evenly at the periphery of the column, each conduit (2) supplying the horizontal distribution channel (3), and the bed of granular solid (5) then being fed from said distribution channel (3) through a screen (4), the fluid flowing through the granular bed (5) in a substantially vertical direction, the fluid then being collected below the screen (6) by means of a collection channel (7), the entire flow being collected into a single evacuation conduit (11) which is centred substantially on the vertical axis of the column, the throughput velocity of the fluid being discharged from the peripheral conduits (8) being in the range 1 to 6 m/s.

6. A process using the distribution or collection device as claimed in claim 3, in which the fluid is introduced into the granular bed from a central conduit (1) which is divided into a plurality of peripheral conduits (2) which are distributed evenly at the periphery of the column, and permitting the granular bed (5) to be fed, the fluid passing through said bed from the periphery towards the centre where it is collected in the central channel (7) and then is evacuated via the conduit (11) which is centred substantially on the vertical axis of the column, the throughput velocity of the fluid entering the peripheral conduits (2) being in the range 1 to 6 m/s.

7. The simulated moving bed separation process using the device as claimed in claim 1, in which the feed to be separated is any mixture of aromatic compounds containing 7 to 9 carbon atoms.

8. The simulated moving bed separation process using the device as claimed in claim 1, in which the feed to be separated is a mixture of normal and iso-paraffins.

9. The simulated moving bed separation process using the device as claimed in claim 1, in which the feed to be separated is a mixture of normal and iso-olefins.

10. The simulated moving bed separation process using the device as claimed in claim 1, in which the principal fluid passing through said device has a density in the range 600 to 950 kg/m$^3$ and a viscosity in the range 0.1 to 0.6 cPo.

* * * * *